United States Patent [19]

Matsuda et al.

[11] Patent Number: 4,970,338
[45] Date of Patent: Nov. 13, 1990

[54] PREPARATION PROCESS OF BIPHENYL-4,4'-DICARBOXYLIC ACID

[75] Inventors: Toshiharu Matsuda, Iwaki; Tadashi Nakamura, Tokyo; Atsushi Sasakawa, Iwaki; Shoichiro Hayashi, Iwaki; Yutaka Konai, Iwaki, all of Japan

[73] Assignee: Kureha Kagaku Kogyo K.K., Japan

[21] Appl. No.: 307,187

[22] Filed: Nov. 30, 1988

Related U.S. Application Data

[63] Continuation of Ser. No. 119,896, Nov. 12, 1987, abandoned.

[30] Foreign Application Priority Data

Nov. 11, 1986 [JP] Japan .................. 61-266641

[51] Int. Cl.$^5$ .......................... C07C 51/255
[52] U.S. Cl. .................................. 562/416
[58] Field of Search ........................ 562/416

[56] References Cited

U.S. PATENT DOCUMENTS

| 3,281,459 | 10/1956 | Serres | 562/416 |
| 4,804,788 | 2/1989 | Konai | 568/730 |

FOREIGN PATENT DOCUMENTS

| 56-156222 | 12/1981 | Japan . |
| 57-16831 | 1/1982 | Japan . |
| 60-174745 | 2/1985 | Japan . |

OTHER PUBLICATIONS

Prostakov, Zr. Prinkl. Khim, 40 pp. 935–936 (1967).
Roberts, "An Introduction to Modern Experimental Organic Chemistry," pp. 35–41 (1969).
Blanchi, C. Paul, Chemical Abstracts, vol. 96, No. 25, p. 705, 96:217480y, "4,4'-Biphenyldicarboxylic acid", Jun. 21, 1982.
Billmeyer, Fred W., Chemical Abstracts, vol. 81, No. 24, p. 420, 159548d, "Preparation of 4,4'-diphenyldicarboxylic acid", Dec. 16, 1974.
Beck, Curt W., Chemical Abstracts, vol. 67, No. 7, p. 3045, 32367z, "Oxidation of p,p'-bitolyl", Aug. 14, 1967.
Ukr, Khim, ZH., 30, 938–941 (1964).

Primary Examiner—Michael L. Shippen
Attorney, Agent, or Firm—Lowe, Price, LeBlanc, Becker & Shur

[57] ABSTRACT

Biphenyl-4,4'-dicarboxylic acid is prepared by isolating a mixture of diisopropylbiphenyls from a reaction mixture obtained by reacting biphenyl with propylene, crystallizing 4,4'-diisopropylbiphenyl from the mixture of diisopropylbiphenyls, and oxidizing 4,4'-diisopropylbiphenyl or an oxidation intermediate thereof with molecular oxygen in the presence of an oxidation catalyst, which comprises a cobalt catalyst and/or manganese catalyst, in a solvent containing at least 50 wt. % of an aliphatic mono-carboxylic acid having up to 3 carbon atoms.

15 Claims, No Drawings

PREPARATION PROCESS OF BIPHENYL-4,4'-DICARBOXYLIC ACID

This application is a continuation of application Ser. No. 119,896, filed Nov. 12, 1987 now abandoned.

BACKGROUND OF THE INVENTION

1. Field of the Invention:

This invention relates to a process for preparing biphenyl-4,4'-dicarboxylic acid by oxidizing 4,4'40-diisopropylbiphenyl or an oxidation intermediate thereof with molecular oxygen. Biphenyl-4,4'-dicarboxylic acid is usful as a raw material for the production of high-performance polyesters and aramid resins having high heat resistance and strength.

heretofore been The following processes have heretofore been known as preparation processes of biphenyl-4,4'-dicarboxylic acid.

(1) 4,4'-Diacetylbiphenyl, which has been obtained by acetylating biphenyl, is oxidized with a hypochlorite [Ukr, Khim, Zh., 30, 938–941 (1964)].

(2) p-Bromotoluene is converted with magnesium into 4,4'-dimethylbiphenyl in ether, followed by oxidation with a cobalt catalyst and bromine catalyst in acetic acid [Zr, Prinkl, Khim, 40, 935 (1967)].

(3) Using iron chloride or aluminum chloride as a catalyst, biphenyl is reacted with a halogenated cyclohexane in nitrobenzene or carbon disulfide as a solvent to form 4,4'-dicyclohexylbiphenyl. It is then oxidized in the presence of a cobalt catalyst, manganese catalyst and bromine catalyst in acetic acid (Japanese Patent Laid-Open No. 16831/1982).

(4) Using $BF_3$ as a catalyst, a 4-alkylbiphenyl is reacted with carbon monoxide in hydrogen fluoride as a solvent to form a 4-alkyl-4'-formylbiphenyl. It is then oxidized in the presence of a cobalt catalyst, manganese catalyst and bromine catalyst in acetic acid (Japanese Patent Laid-Open No. 174745/1985).

These conventional processes are however accompanied by the following problems.

The process (1) requires, as a catalyst for the acetylation, a great deal of aluminum chloride which is difficult to regenerate and is highly corrosive. In addition, the oxidation with the hypochlorite induces significant corrosion. It is hence difficult to practise this process industrially.

The process (2) obtains the starting material, 4,4'-diacetylbiphenyl, by a Grignard reaction which consumes expensive magnesium. This process is thus impractical.

The process (3) obtains the starting material, 4,4'-dicyclohexylbiphenyl by using iron chloride, aluminum chloride or the like, which is difficult to regenerate and is highly corrosive, as a catalyst like the process (1) and by employing as a solvent nitrobenzene or carbon disulfide which is very dangerous due to its high inflammability and toxicity. Its industrial practice is therefore very troublesome. Moreover, oxidation of the starting material results in an oxidative loss of the expensive cyclohexyl groups. It is hence difficult to practise this process industrially.

The process (4) makes use of hydrogen fluoride and $BF_3$, which are very corrosive, in order to obtain the starting material, i.e., the 4-alkyl-4'-formylbiphenyl. It is therefore necessary to use an expensive and corrosion-resistant reactor. This process is accompanied by another drawback that the purification of the resulting product is cumbersome, since di-substituted derivatives other than 4,4'-derivative are also formed.

The above-described processes, which have heretofore been proposed as processes for the preparation of biphenyl-4,4'-dicarboxylic acid, are accompanied by their own drawbacks. A great deal of effrts has been exercised to overcome such drawbacks. No satisfactory effects have however been achieved to date. Accordingly, the high price of biphenyl-4,4'-dicarboxylic acid still remains as an obstacle for the expansion of its application field.

SUMMARY OF THE INVENTION

An object of this invention is to overcome the above-mentioned drawbacks of the prior art in the preparation of biphenyl-4,4'-dicarboxylic acid by oxidation of a biphenyl derivative with molecular oxygen, thereby to provide a preparation process of biphenyl-4,4'-dicarboxylic acid in which the starting biphenyl derivative is available readily and biphenyl-4,4'-dicarboxylic acid is obtained in a high yield and in a form permitting easy purification.

The above object of this invention can be attained by using 4,4'-diisopropylbiphenyl or an oxidation intermediate thereof as a starting biphenyl derivative and oxidizing same with molecular oxygen under specific reaction conditions.

Namely, the present invention relates to a process for the preparation of biphenyl-4,4'-dicarboxylic acid, which comprises oxidizing 4,4'-di-isopropyl-biphenyl or an oxidation intermediate thereof with molecular oxygen in the presence of an oxidation caaalyst, which comprises a cobalt catalyst and/or manganese catalyst, in a solvent containing at least 50 wt.% of an aliphatic monocarboxylic acid having up to 3 carbon atoms.

According to the process of this invention, readily-available 4,4'-diisopropylbiphenyl or an oxidation intermediate thereof can be used as a starting material. Moreover, biphenyl-4,4'-dicarboxylic acid can be obtained in a high yield with less formation of byproducts.

In the process of this invention, use of the heavy metal catalyst or catalysts in combination with a bromine catalyst can activate the oxidative reaction further.

DETAILED DESCRIPTION OF THE INVENTION

Certain features of the present invention will hereinafter be described in detail. (4,4'-diisopropylbiphenyl and its oxidation intermediates)

The starting material useful in the practice of this invention, namely, 4,4'-diisopropylbiphenyl can be easily obtained as a product of a purity as high as 99.8% or higher by distilling and separating diisopropylbiphenyls from a reaction mixture, which has been obtained by subjecting biphenyl to propylation and transalkylation by a method known per se in the art and has a high diisopropylbiphenyl content, and then crystallizing and isolating 4,4'-diisopropylbiphenyl alone from the diisopropylbiphenyls in accordance with differences in crystallinity.

In the course of an investigation on the preparation of 4,4'-dialkyl-substituted biphenyls which can be derived at a low cost from biphenyl and can be separated easily from other isomers byproduced, the present inventors previously found that 4,4'-diisopropylbiphenyl can be obtained by reacting biphenyl and propylene in the presence of a silica-alumina catalyst.

It has conventionally been impossible to isolate a 4,4'-dialkylbiphenyl alone from corresponding dialkylbiphenyls formed by introducing a corresponding lower alkyl group such as methyl or ethyl group through an alkylation reaction, because the boiling points of these isomers are too close to permit their separation by distillation and they have no substantial differences in crystallinity, thereby making it difficult to separate them by crystallization.

When isopropyl group, an alkyl group having a branched structure, is introduced in biphenyl, substituted derivatives other than the 4,4'-di-substituted derivative are all poor in crystallinity due to steric hindrance and are each in an oily or low m.p. solid form. In contrast, 4,4'-diisopropylbiphenyl has little steric hindrance. Accordingly, its crystallinity is good and its melting point is as high as 64–65° C. It can therefore be separated easily from the reaction mixture.

The above-described Japanese Patent Laid-Open No. 16831/1982 discloses that 4,4'-dicyclohexylbiphenyl is good in crystallinity and is hence convenient for separation. When biphenyl-4,4'-dicarboxylic acid is prepared by oxidizing this 4,4'-dicyclohexylbiphenyl, ten carbon atoms are however wasted per molecule of 4,4'-dicyclohexylbiphenyl in the course of the oxidative reaction. On the other hand, the present invention makes use of 4,4'-diisopropylbiphenyl as a starting material, thereby bringing about a merit that the loss of carbon atoms in the oxidative reaction has been reduced to only 4 carbon atoms per molecule of 4,4'-diisopropylbiphenyl.

The term "oxidation intermediate of 4,4'-diisopropylbiphenyl" as used herein means a derivative formed by oxidation of 4,4'-diisopropylbiphenyl. It is an oxidation derivative which affords biphenyl-4,4'-dicarboxylic acid upon further oxidation in the reaction system. As its preferable example, 4'-isopropylbiphenyl-4-carboxylic acid may be mentioned. 4'-Isopropylbiphenyl-4-carboxylic acid is a compound having a molecular weight of 240.3 and a melting point of 234.5°–235.2° C., and is obtained by oxidizing 4,4'-diisopropylbiphenyl with molecular oxygen in the presence of a cobalt catalyst and/or manganese catalyst in a solvent of an aliphatic monocarboxylic acid having up to 3 carbon atoms.

Needless to say, it has not been known to prepare biphenyl-4,4'-dicarboxylic acid by oxidizing 4,4'-diisopropylbiphenyl or an oxidation intermediate thereof with molecular oxygen.

(Solvent)

The solvent useful in the practice of this invention is a solvent containing at least 50 wt.% of an aliphatic monocarboxylic acid having up to 3 carbon atoms.

Illustrative examples of the aliphatic monocarboxylic acid having up to 3 carbon atoms may include formic acid, acetic acid and propionic acid, with acetic acid being particularly preferred.

The solvent to be used may be mixed with water, an aldehyde such as paraformaldehyde, or ketone such as methyl ethyl ketone as needed. When water is used, its proportion may preferably be 30 wt.% or lower. When an aldehyde or ketone is employed, it is preferable to limit its proportion to 10 wt.% or less.

It is preferable to use the solvent in an amount of about 2–20 times by weight as much as the total amount of the starting material, i.e., 4,4'-di-isopropylbiphenyl or an oxidation intermediate thereof and the resulting desired compound, i.e., biphenyl-4,4'-dicarboxylic acid. If the solvent should be used in an excessively small amount, the flowability of the reaction system will be reduced to hamper the smooth reaction. Even if the solvent should be used in any large amounts in excess of the upper limit on the contrary, the reaction itself will not be accelerated. It is hence not beneficial to use the solvent in such a large excess amount.

(Oxidation catalysts)

The cobalt catalyst and manganese catalyst useful in the practice of this invention may be either metals or compounds so long as they are in forms soluble in the oxidative reaction system. No particular limitation is imposed thereon. As specific examples, may be mentioned the inorganic salts of cobalt and manganese such as their oxides, hydroxides, carbonates, basic carbonates and halides, the salts of cobalt and manganese and organic carboxylic acids such as formic acid, acetic acid, propionic acid, naphthenic acid and aromatic carboxylic acids. Of these, their bromides and fatty acid salts are preferred with their acetates being particularly preferred.

Although the cobalt catalyst and manganese catalyst may be used singly, they may be used in combination.

It is preferable to use the cobalt catalyst and/or manganese catalyst in a total amount of 0.001 gram atom or more in terms of metal element(s) per 100 gram of the solvent. The selectivity to biphenyl-4,4'-dicarboxylic acid and its oxidation intermediates is improved further as these oxidation catalysts are used in greater amounts.

The upper limit to the total amount of the cobalt catalyst and/or manganese catalyst to be used varies depending on their solubilities to the solvent. No significant improvement is however observed to the selectivity even if the catalyst(s) are used in any total amount greater than 0.2 gram atom in terms of metal element(s) per 100 g of the solvent. It is hence economically disadvantageous to use the catalyst(s) in such an excess amount.

By the way, the total selectivity to oxidation intermediates and biphenyl-4,4'-dicarboxylic acid is improved as mentioned above, for example, to 95% or higher when the total amount, namely, total concentration of the cobalt catalyst and/or manganese catalyst increases. On the other hand, a fact is observed that the velocity of formation of biphenyl-4,4'-dicarboxylic acid is rendered slower.

The present inventor has hence proceeded with a further investigation. As a result, it has also been found that biphenyl-4,4'-dicarboxylic acid can be formed at a high selectivity and a high formation velocity when a compound capable of yielding bromine ions is used as an additional oxidation catalyst in combination with the cobalt catalyst and/or manganese catalyst.

As illustrative examples of the compound which can yield bromine ions and is employed as the additional oxidation catalyst, may be mentioned inorganic substances such as molecular bromine, hydrogen bromide and hydrobromides as well as organic compounds such as ethyl bromide and bromoacetic acid. Although no particular limitation is imposed so long as the compound is dissolved in the oxidative reaction system to yield bromine ions, hydrogen bromide, potassium bromide and ammonium bromide are preferred.

The above bromine compound may be added to the reaction system from the beginning. As an alternative, when 4,4'-diisopropylbiphenyl is used as a starting material, it may be added either at once or gradually to the reaction system after the formation of an oxidation intermediate.

The bromine compound may be added in an amount of $1 \times 10^{-4}$ gram atom–$4 \times 10^{-2}$ gram atom in terms of bromine element per 100 grams of the solvent. If the amount of the bromine compound should be smaller than $1 \times 10^{-4}$ gram atom in terms of bromine element, the velocity of formation of biphenyl-4,4'-dicarboxylic acid by the oxidation reaction will be slow. On the other hand, any amounts greater than $4 \times 10^{-2}$ gram atom will result in an increase to the formation of byproducts having one or more bromine atoms bonded on the biphenyl ring, so that the purification of biphenyl-4,4'-dicarboxylic acid from the reaction mixture will be rendered difficult.

(Reaction conditions)

Although the starting material, namely, 4,4'-diisopropylbiphenyl may be added to at once the oxidative reaction system containing the solvent and oxidation catalyst(s), still better results may be obtained when it is added gradually at a predetermined feeding rate.

Since the tertiary hydrogen atoms in the two isopropyl groups of 4,4'-diisopropylbiphenyl are active, the hydrogen abstraction reaction as the first stage of the oxidative reaction proceeds easily. The velocity of the abstraction reaction of the tertiary hydrogen atoms in the two isopropyl groups of 4,4'-diisopropylbiphenyl is faster than the velocity of formation of the desired compound, i.e., biphenyl-4,4'-dicarboxylic acid. If the feeding rate of 4,4'-diisoproylbiphenyl to the oxidative reaction system is too high, it is estimated that the concentrations of reaction products in some intermediate stages of the oxidation would increase and when their concentrations exceed certain levels, a side reaction would be induced to form a polycondensation product and the yield of the desired compound would be lowered correspondingly.

The existence of an important causal relation is therefore recognized between the feeding rate of 4,4'-diisopropylbiphenyl to the oxidative reaction system and the yield of biphenyl-4,4'-dicarboxylic acid.

The feeding rate of 4,4'-diisopropylbiphenyl to the oxidative reaction system may preferably be in a range from of 0.01 gram mole to 1.5 gram moles per hour and per kg of the total weight of the catalyst(s) and solvent in the reactor. Any feeding rates smaller than 0.01 gram mole per hour are impactical because a large reactor is required. On the other hand, any feeding rates greater than 1.5 gram moles per hour result in an increase of the formation of byproducts due to side reactions, thereby lowering the yield of the desired compound.

The reaction temperature may preferably range from 100° C. to 240° C. Any temperatures lower than the lower limit result in a slow reaction velocity, while any temperatures higher than the upper limit lead to more oxidative decomposition of the solvent. It is hence not preferable to use any reaction temperature outside the above range.

The pressure of the oxidative reaction system may be at any level, so long as the solvent is allowed to remain in a liquid phase at the reaction temperature. As the oxygen partial pressure, 0.1–8 kg/cm$^2$-abs. is sufficient. In the case of molecular oxygen diluted with an inert gas, for example, air, a range of 0–30 kg/cm$^2$-G is sufficient as its total pressure.

ADVANTAGES OF THE INVENTION

The process of this invention for the preparation of biphenyl-4,4'-dicarboxylic acid is superior in that it has both of the following merits:

(1) The preparation of its starting material, i.e., 4,4'-diisopropylbiphenyl or its oxidation intermediate is easy; and (2) The reaction product is practically free of biphenyldicarboxylic acids other than the 4,4'-derivative and the purification of the intended compound is easy.

The preparation process of this invention is therefore useful in the industry.

EMBODIMENTS OF THE INVENTION

The present invention will hereinafter be described in detail by the following Examples. It should however be borne in mind that the present invention is not necessarily limited to the following Examples.

Example 1:

Five experiments were conducted separately by varying the kind and amount of the catalyst and reaction time as shown in Table 1.

In each experiment, 10 g of 4,4'-diisopropylbiphenyl, 100 g of glacial acetic acid and the corresponding amount(s) of the corresponding catalyst(s) were charged in a 200-cc autoclave made of titanium. The contents were stirred vigorously at 180° C. while maintaining the pressure at 15 kg/cm$^2$-G Air was fed at a rate of 24 l (STP) per hour.

After proceeding with the reaction for a predetermined period of time, the reaction mixture was cooled. Biphenyl-4,4'-dicarboxylic acid which had crystallized out was collected by filtration and washed with hot acetic acid and then with water, whereby biphenyl-4,4'-dicarboxylic acid was isolated. The filtered cake and filtrate were also analyzed to obtain results shown in Table 1.

From Table 1, it is appreciated that the total selectivity to 4'-isopropylbiphenyl-4-carboxylic acid, an oxidation intermediate, and biphenyl-4,4'-dicarboxylic acid reaches as high as 95% or even higher when the cobalt and manganese catalysts are used in large amounts. It is also understood that the unreacted starting material and the oxidation intermediate are eliminated and are converted into biphenyl-4,4'-dicarboxylic acid in a short period of time by an addition of a bromine compound.

TABLE 1

|  | Experiment No. |  | 1 | 2 | 3 | 4 | 5 |
| --- | --- | --- | --- | --- | --- | --- | --- |
| Catalyst | Co(OAc)$_2$.4H$_2$O | g | 0.5 | 15.4 | 5.0 | 0.5 | 6.4 |
|  | Mn(OAc)$_2$.4H$_2$O | g | 1.0 | — | 15.0 | 1.0 | 18.9 |
|  | NH$_4$Br | g | — | — | — | 0.05 | 1.0 |
|  | Reaction time | hr | 2.5 | 2.5 | 2.5 | 2.0 | 2.0 |
|  | Weight of filter cake | g | 5.68 | 7.67 | 3.0 | 5.73 | 6.65 |
| Yield | Unreacted starting material | mol % | 0.6 | — | 24.3 | — | — |
|  | BPMC | mol % | 40.0 | 15.9 | 65.7 | — | — |

TABLE 1-continued

| Experiment No. | | 1 | 2 | 3 | 4 | 5 |
|---|---|---|---|---|---|---|
| BPDC | mol % | 29.4 | 33.0 | 6.4 | 35.8 | 32.5 |

BPMC: 4'-isopropylbiphenyl-4-carboxylic acid.
BPDC: biphenyl-4,4'-dicarboxylic acid.

Example 2

Charged in a 5l autoclave made of titanim were 2,380 g of glacial acetic acid, 12 g of cobalt acetate tetrahydrate and 24 g of manganese acetate tetrahydrate. While stirring the contents vigorously, air was fed at 190° C. and 15 kg/cm$^2$-G at a rate of 600 l (STP) per hour. Into the autoclave, 238 g of 4,4'-diisopropylbiphenyl was fed in the course of 3 hours. After the feeding of the starting material, air was introduced at the same temperature and pressure for additional 2 hours. At that time, the feeding rate of 4,4'-diisopropylbiphenyl was 0.14 gram mole per hour and per kg of the total weight of the catalysts and acetic acid in the autoclave. After the reaction, the reaction mixture was cooled and filtered. The filtered cake was washed with hot acetic acid and then with water, thereby obtaining 190 g of crude biphenyl-4,4'-dicarboxylic acid whose purity was 93.6%. The yield was 73.5%. Here, 36 g of 4'-isopropyl-biphenyl-4carboxylic acid was contained in total in the filtrate and washing.

Example 3

Charged in a 5; autoclave made of titanium were 1,190 g of glacial acetic acid, 76 g of cobalt acetate tetrahydrate, 225 g of manganese acetate tetrahydrate and 12 g of ammonium bromide.

While stirring the contents vigorously, air was fed at 180° C. and 9 kg/cm$^2$-G at a rate of 1,200 l (STP) per hour.

Into the autoclave, 238 g of 4,4'-diisopropylbiphenyl was fed in the course of 1 hour. After the feeding of the starting material, air was introduced at the same temperature and pressure for additional 2 hours. At that time, the feeding rate of 4,4'-diisopropylbiphenyl was 0.67 gram mole per hour and per kg of the total weight of the catalysts and acetic acid in the autoclave. After the reaction, the reaction mixture was cooled down to 100° C. and filtered. The filtered cake was washed with hot acetic acid and then with water, thereby obtaining 230 g of crude biphenyl-4,4'-dicarboxylic acid whose purity was 95%. The yield was 90.3%.

What is claimed is:

1. A high yield method for the preparation of biphenyl-4,4'-dicarboxylic acid, comprising
   oxidizing %b 4,4'-dissopropylbiphenyl in an oxidation reactor with molecular oxygen in a solvent comprising at least 50 wt% of a (C$_1$–C$_3$)aliphatic monocarboxylic acid in the presence of 0.001–0.2 gram atoms metal element of at least one oxidation catalyst selected from the group consisting of cobalt catalysts and manganese catalysts per 100 g solvent, and 1×10$^{-4}$ to 4×10$^{-2}$ atoms bromine per gram of a bromine ion-producing catalyst per 100 g solvent at a temperature of 100°–240° C., a partial pressure of oxygen of 0.1–8 kg/cm$^2$-abs., and a 4,4'-diisopropylbiphenyl feeding rate of 0.01–1.5 gram moles/hour per kilogram of total amount of catalyst and solvent.

2. The method of claim 1, wherein
   the oxidation catalyst comprises a cobalt catalyst and a manganese catalyst.

3. The method of claim 1, wherein
   the oxidation solvent further comprises up to 30 wt% water, or up to 10 wt% of an aldehyde or a ketone.

4. The method of claim 1, wherein
   the proportion of oxidation solvent: 4,4'-biphenyl is about 2:1 to 20:1 by weight.

5. The method of claim 1, wherein
   the oxidation catalyst is selected from the group consisting of oxides, hydroxides, carbonates, basic carbonates and halides of cobalt and manganese and the salts of cobalt and manganese and organic carboxylic acids selected from the group consisting of formic acid, acetic acid, propionic acid, and aromatic carboxylic acids.

6. The method of claim 5, wherein
   the oxidation catalyst is selected from the group consisting of bromide salts of cobalt and manganese, and fatty acid salts of cobalt and manganese.

7. The method of claim 1, wherein
   the oxidation step is conducted in the presence of an inert gas comprising oxygen under a total pressure of 0 to about 30 kg/cm$^2$-G.

8. A high yield method for the preparation of biphenyl 4,4'dicarboxyoxylic acid, comprising
   reacting biphenyl with propylene in the presence of a catalyst under conditions effective to obtain a mixture of diisopropylbinphenyls;
   transalkylating the diisopropylbiphenyls to obtain an increase in content of 4,4'-diisopropylbiphenyl;
   separating the mixture of diisopropylbiphenyls from the reaction mixture;
   crystallizing the 4,4'-diisopropylbiphenyl from the mixture of diisopropylbiphenyls; and
   oxidizizing 4,4'-diisopropylbiphenyl in an oxidation reactor with molecular oxygen in a solvent comprising at least 50 wt% of a (C$_1$–C$_3$)aliphatic monocarboxylic acid in the presence of 0.001–0.2 gram atoms metal element of at least one oxidation catalyst selected from the group consisting of cobalt catalysts and manganese catalysts per 100 g solvent and 1×10$^{-4}$ to 4×10$^{-2}$ atoms bromine per gram of a bromine ion-producing catalyst per 100 g solvent at a temperature of 100°–240° C., a partial pressure of oxygen of 0.1–8 kg/cm$^2$-abs., and a 4,4'-diisopropylbiphenyl feeding rate of 0.01–1.5 gram moles/hour per kilogram of total amount of catalyst and solvent.

9. The method of claim 8, wherein
   the oxidation catalyst comprises a cobalt catalyst and a manganese catalyst.

10. The method of claim 8, wherein
    the catalyst for the reaction of biphenyl with propylene is a silica-alumina catalyst.

11. The method of claim 8, wherein
    the oxidation solvent further comprises up to 30 wt% water, or up to 10 wt% of an aldehyde or a ketone.

12. The method of claim 8, wherein
    the proportion of oxidation solvent:4,4'-biphenyl is about 2:1 to 20:1 by weight.

13. The method of claim 8, wherein
the oxidation catalyst is selected from the group consisting of oxides, hydroxides, carbonates, basic carbonates and halides of cobalt and manganese and the salts of cobalt and manganese and organic carboxylic acids selected from the group consisting of formic acid, acetic acid, propionic acid, and aromatic carboxylic acids.

14. The method of claim 13, wherein
the oxidation catalyst is selected from the group consisting of bromide salts of cobalt and manganese, and fatty acid salts of cobalt and manganese.

15. The method of claim 7, wherein
the oxidation step is conducted in the presence of an inert gas comprising oxygen under a total pressure of 0 to about 30 kg/cm$^2$-G.

* * * * *

UNITED STATES PATENT AND TRADEMARK OFFICE
CERTIFICATE OF CORRECTION

PATENT NO. : 4,970,338

DATED : November 13, 1990

INVENTOR(S) : Matsuda et al.

It is certified that error appears in the above-identified patent and that said Letters Patent is hereby corrected as shown below:

Column 1, line 11, "4,4'40-di-" should be --4,4'-di-- line 17, "heretofore been The following processes have here" should be --2. Related art:

The following processes have here--

Column 2, line 32, "caaalyst" should be --catalyst--

Column 6, line 39, "15 kg/cm$^2$-G Air" should be --15 kg/cm$^2$ G. Air--

Column 7, line 54, "oxidizing %b 4,4'-dissopropylbiphenyl" should be --oxidizing 4,4'-diisopropylbiphenyl--

Signed and Sealed this

Twenty-first Day of April, 1992

Attest:

HARRY F. MANBECK, JR.

*Attesting Officer*          *Commissioner of Patents and Trademarks*